(12) United States Patent
Rensch et al.

(10) Patent No.: US 10,525,466 B2
(45) Date of Patent: Jan. 7, 2020

(54) COMPACT VALVE ARRAY WITH ACTUATION SYSTEM

(71) Applicant: General Electric Company, Schenectady, NY (US)

(72) Inventors: Christian Friedrich Peter Rensch, Munich (DE); Victor Donald Samper, Kirchseeon (DE); Ruben Julian Salvamoser, Munich (DE)

(73) Assignee: General Electric Company, Schenectady, NY (US)

( * ) Notice: Subject to any disclaimer, the term of this patent is extended or adjusted under 35 U.S.C. 154(b) by 366 days.

(21) Appl. No.: 15/267,479

(22) Filed: Sep. 16, 2016

(65) Prior Publication Data

US 2018/0078937 A1    Mar. 22, 2018

(51) Int. Cl.
*B01L 3/00* (2006.01)
*G01N 35/10* (2006.01)
*F16K 99/00* (2006.01)
*G01N 35/00* (2006.01)

(52) U.S. Cl.
CPC ..... *B01L 3/502715* (2013.01); *B01L 3/50273* (2013.01); *B01L 3/502738* (2013.01); *F16K 99/0015* (2013.01); *F16K 99/0055* (2013.01); *G01N 35/10* (2013.01); *B01L 2200/025* (2013.01); *B01L 2200/027* (2013.01); *B01L 2200/0689* (2013.01); *B01L 2200/12* (2013.01); *B01L 2300/0829* (2013.01); *B01L 2300/0887* (2013.01); *B01L 2300/123* (2013.01); *B01L 2300/14* (2013.01); *B01L 2400/0478* (2013.01); *B01L 2400/0622* (2013.01); *B01L 2400/0638* (2013.01); *B01L 2400/0655* (2013.01);

(Continued)

(58) Field of Classification Search
CPC ......... B01L 3/502715; B01L 3/502738; B01L 3/50273; B01L 2300/0829; B01L 2300/123; B01L 2200/12; B01L 2300/0887; B01L 2400/0655; B01L 2200/025; B01L 2200/0689; B01L 2200/027; B01L 2300/14; B01L 2400/0478; B01L 2400/0638; B01L 2400/0622; F16K 99/0055; F16K 99/0015; G01N 35/10; G01N 2035/00247; G01N 2035/1044
See application file for complete search history.

(56) References Cited

U.S. PATENT DOCUMENTS

| 4,274,452 A | 6/1981 | Schmitt |
| 4,872,638 A | 10/1989 | Thompson et al. |
| 4,991,548 A | 2/1991 | Richeson et al. |

(Continued)

FOREIGN PATENT DOCUMENTS

| CN | 2578620 Y | 10/2003 |
| WO | 97/27324 A1 | 7/1997 |

OTHER PUBLICATIONS

International Search Report and Written Opinion issued in connection with corresponding PCT Application No. PCT/US2017/050166 dated Nov. 13, 2017.

(Continued)

*Primary Examiner* — Samuel P Siefke

(57) ABSTRACT

Described herein is a system for on-demand synthesis/analysis of compounds and/or diagnostic applications. In general, any application that requires a low-cost binary switch valve array for fast (<100 ms) switching of gases or liquids, in a spatially compact format, is compatible with the system described herein.

20 Claims, 8 Drawing Sheets

(52) U.S. Cl.
CPC .............. *G01N 2035/00247* (2013.01); *G01N 2035/1044* (2013.01)

(56) References Cited

U.S. PATENT DOCUMENTS

| | | |
|---|---|---|
| 6,003,481 A | 12/1999 | Pischinger et al. |
| 2012/0267561 A1 | 10/2012 | Samper et al. |
| 2014/0050635 A1 | 2/2014 | Azzi et al. |
| 2014/0213757 A1 | 7/2014 | Shales et al. |
| 2015/0204450 A1 | 7/2015 | Tuccelli et al. |

OTHER PUBLICATIONS

Boeld, D., et al., Microvalve, GE co-pending U.S. Appl. No. 61/291,464, filed Dec. 31, 2009.

Kawai et al.,"Nomally-closed valve integration for pneumatic actuators", Solid-State Sensors, Actuators and Microsystems (Transducers & Eurosensors XXVII), 2013 Transducers & Eurosensors XXVII: The 17th International Conference on, pp. 254-257, Jun. 16-20, 2013, Barcelona.

Ma et al.,"Characteristics Analysis and Testing of SMA Spring Actuator", Advances in Materials Science and Engineering, vol. 2013, pp. 7, 2013.

Rensch et al., "Microfluidics: a groundbreaking technology for PET tracer production? molecules", Molecules 2013, 18(7), pp. 7930-7956, Jul. 5, 2013.

Rensch et al.,"A solvent resistant lab-on-chip platform for radiochemistry applications.", Lab Chip, 14(14), pp. 2556-2564, Jul. 21, 2014.

Comecer S.p.A., "BBS Combo Series—Synthesis and Dispensing Hot Cell" https://www.comecer.com/nuclear-medicine/radiochemistry-pet-cyclotron-conventional-nuclear-medicine/hot-cells/bbst-combo-series-synthesis-and-dispensing-hot-cell/, Retrieved on Oct. 17, 2015.

COMPACT VALVE ARRAY WITH ACTUATION SYSTEM

BACKGROUND

The present disclosure is related to the field of miniature- and microfluidics. More specifically, the present disclosure relates to a system comprising an array of fluidic binary switches which enables manipulation of liquids and gases within a three-dimensional channel network. The fluidic binary switch array is composed of reusable and disposable elements, where only the disposable element is exposed to process fluids. Further, the disposable element is designed to be easily and quickly replaced without the need for tools, either by a human or by simple linear automation.

Many chemical and biochemical processing applications make use of single-use disposables to simplify production and ensure the quality of the product. Disposables help achieve this by reducing or avoiding the need for steps such as system set-up verification and validation, cleaning, and cleaning validation. Only process liquids and the final product are exposed to the disposable elements. While disposables simplify the procedure of achieving and maintaining quality in the chemical or biochemical process, the disposable components and the systems that interface with the disposable components are challenging to manufacture/assemble without incurring prohibitive cost from complex structures, materials, or manufacturing processes. An example of a single-use disposable in industrial bioprocessing is the GE Healthcare Life Sciences ReadyToProcess WAVE 25 cell culture device. An example of a single-use disposable in radiopharmaceutical preparation is the GE Healthcare FASTlab cassette for synthesis of Positron Emission Tomography (PET) tracers such as Fluorodeoxyglucose (FDG).

In procedures requiring multiple chemical steps, such as Positron Emission Tomography (PET) tracer synthesis, rotary stop-cock valves and tubing pinch valves are used, with rotary stop-cock valves being the most common. Rotary stop-cock valves are found either as individual pieces, or as an integrated serial bank. In the case of integrated serial banks, valve arrays consisting of 25 or more valves connected in series, are manufactured as a single part, to reduce the number of individual parts requiring assembly. The valves provide process fluid control and are one of the critical components in the disposable element. The valves are connected to the other required components, such as pumps, filters, and reactors, via tubing and fittings.

The combination of rotary valves, other essential components such as pumps, filters, and reactors, and tubing, results in the complete disposable. This disposable, together with reagents, is referred to as the disposable kit. These kits have proven to be successful however the use of tubing and the serial connection of valves in banks for use as a single component, has limitations. Assembly of tubing with fittings and other parts is a difficult process to automate, and the applications utilizing the described disposables often do not have the manufacturing volumes to justify investment into the automation of the tubing into the assemblies. This means that the tubing is assembled by hand. The use of serial valve banks to reduce the number of individual parts in the assembly limits the overall flexibility in the routing of fluids, which can lead to undesirable or non-intuitive routing of fluids to avoid cross-contamination. Furthermore, dead-volumes tend to be difficult to reduce due to the limitations of the components and their need to be suitable for assembly by hand. Reduction of dead-volumes is essential in applications that use expensive compounds, where there is a trend to process volumes as small as possible.

Miniature- and micro-fluidics, and integrated manifolds are technologies that reduce or eliminate the use of tubing, however there is a need in the field for robust physical interfaces between components in disposable kits.

BRIEF DESCRIPTION

Described herein is a system for fluidic control and processing on a disposable component, useful for synthesis, analysis, and other applications requiring chemical processing of materials. In general, any application that requires a low-cost binary switch valve array for fast (<100 ms) switching of gases or liquids, in a spatially compact format, is compatible with the system described herein. The system comprises a disposable, miniature, switch array that consists of four functional elements: a disposable polymer substrate with membrane valves densely integrated on its surface; a re-usable integrated pneumatic solenoid plunger array that is used to actuate the valves individually; a connector array that interfaces the disposable polymer substrate to sources and sinks of material needed for the process, and a damping layer that sits between the valve array and the plunger array and is used to soften impact forces from the actuators in order to increase the lifetime of the disposable valve array. The plunger array is a single piece that utilizes one pneumatic feed line that is distributed to all plungers, and individual electrical connections to each plunger solenoid. Under failure situations where the disposable leaks, the damping film is also a shield that isolates and protects the plunger array from chemical leakage.

DRAWINGS

These and other features, aspects, and advantages of the present invention will become better understood when the following detailed description is read with reference to the accompanying drawings in which like characters represent like parts throughout the drawings, wherein:

FIG. 1 shows a computer-aided design (CAD) rendering of the valve actuator block 1 with plungers 2, the damping layer 3 and the disposable monolithic chip 4.

FIG. 2 shows a CAD rendering of the system described herein comprising the disposable monolithic chip in a guiding slot 6, and a connector plate 5 with connectors 9 disposed thereon.

Figure 8:
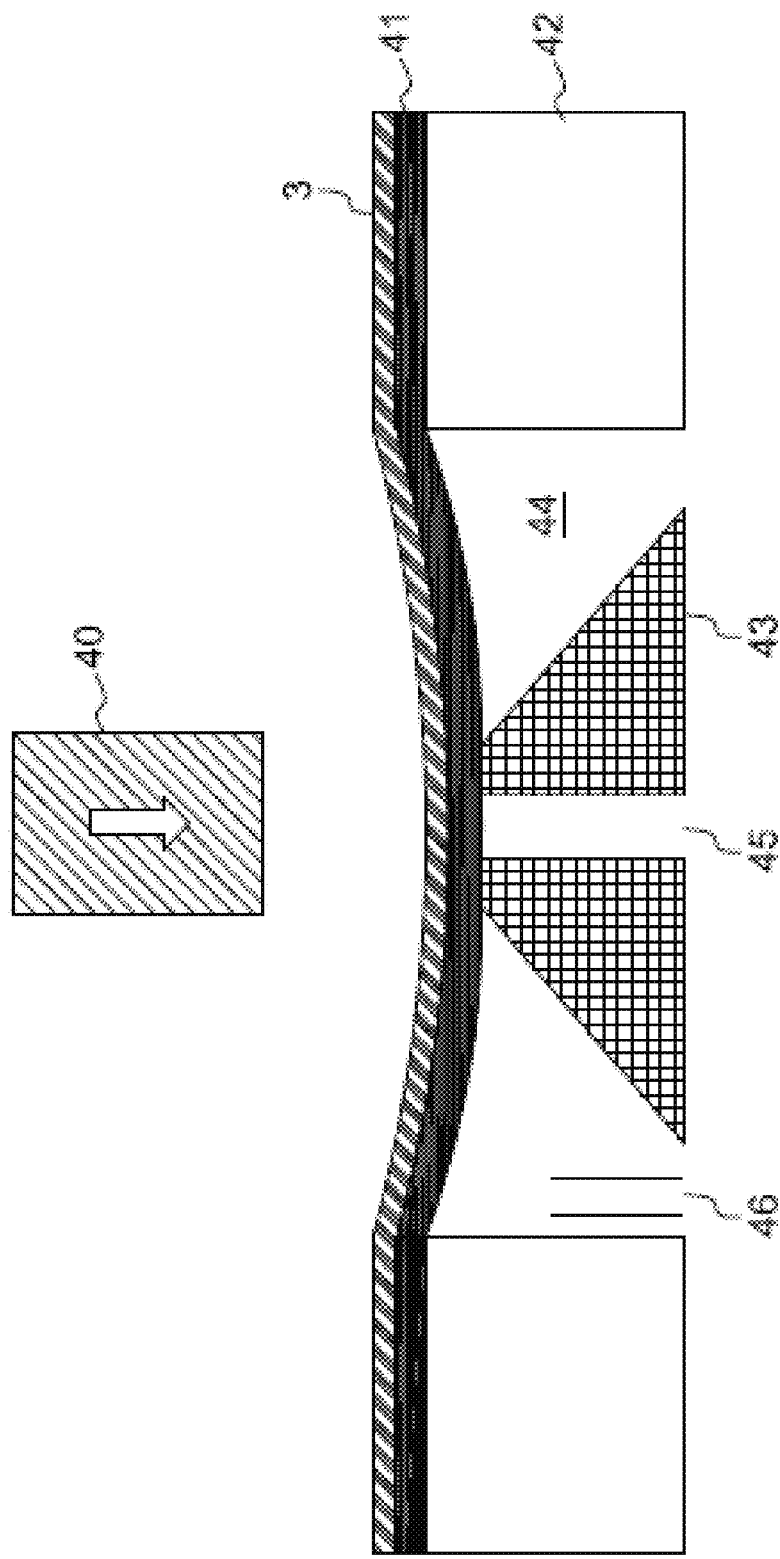

FIG. 8 shows an individual valve 10 in the array which can be operated by a plunger 40 that presses the damping layer 3 towards, and membrane 41 against, valve seat 43.

DETAILED DESCRIPTION

Described herein are systems and methods for automation of fluidic processes which typically comprise multiple steps, e.g., synthesis of compound, purification or isolation of analytes from several samples in parallel, and the like. The system comprises a fluidic binary switch array enabling manipulation of fluids within a three-dimensional channel network and is designed to allow fast and easy installation.

The system comprises a disposable valve array, and its combination with a spatially-dense electro-pneumatic actuator array and a damping layer. By reducing the number of structured components down to a single monolithic/compound piece, formed by irreversibly bonding 1 or more injection molded elements with a deformable foil, the disposable valve array chip can be manufactured at a low cost. The foil can be from the same polymer or a different polymer. The ability to construct the disposable component from one material or family of materials, reduces cost, increases reliability, and opens up demanding (and regulatory controlled) applications such as on-demand synthesis of injectable pharmaceutical compounds. The dense electro-pneumatic actuator array provides suitable actuation forces without placing limiting demands on the density of the disposable valve elements. The valve array is scalable from individual valves to large arrays, is tolerant to a wide range of process fluids and process conditions, is compact, and is more dynamic in its switching behavior compared to conventional rotary valves found in other systems.

Accordingly, the high valve density and fast valve dynamics achieved by utilizing an electro-pneumatic actuator array, the extended life achieved by incorporating a damping sheet between the valve plungers and the disposable valve array, the low dead volumes achieved by using microfluidic valve designs and integrated fluid interconnects, the positive and negative (relative to external pressure) switching capability of the valve due to its dimensions and materials confer process improvements over existing systems. The disposable component is the only component that is in contact with the process gases or liquids. This eliminates cross-contamination from run to run where the disposable is replaced each time thereby improving process reliability. Further, the disposable component can be gamma sterilized after fabrication in a single step, or heat sterilized during fabrication due to the high temperatures used for molding and certain types of foil bonding.

The singular forms "a", "an" and "the" include plural references unless the context clearly dictates otherwise. As used herein, the term "or" is not meant to be exclusive, and refers to at least one of the referenced components being present and includes instances in which a combination of the referenced components may be present, unless the context clearly dictates otherwise.

Approximating language, as used herein throughout the specification and claims, may be applied to modify any quantitative representation that could permissibly vary without resulting in a change in the basic function to which it is related. Accordingly, a value modified by a term or terms, such as "about", and "substantially" are not to be limited to the precise value specified. In some instances, the approximating language may correspond to the precision of an instrument for measuring the value. Here and throughout the specification and claims, range limitations include all the sub-ranges contained therein unless context or language indicates otherwise.

In one aspect, provided herein is a fluidic binary switch system comprised of:
  (i) a valve actuator block attached to a fixture and comprising a two-dimensional array of plungers, each plunger having a corresponding individually addressable actuator;
  (ii) a disposable monolithic chip positioned in a guiding slot on the fixture and comprising (a) a two-dimensional array of membrane valves;
  (b) interconnecting channels among the membrane valves; and
  (c) fluidic ports for the membrane valves;
wherein the fixture aligns the plungers in the valve actuator block with corresponding membrane valves in the monolithic chip.

Figure 1:
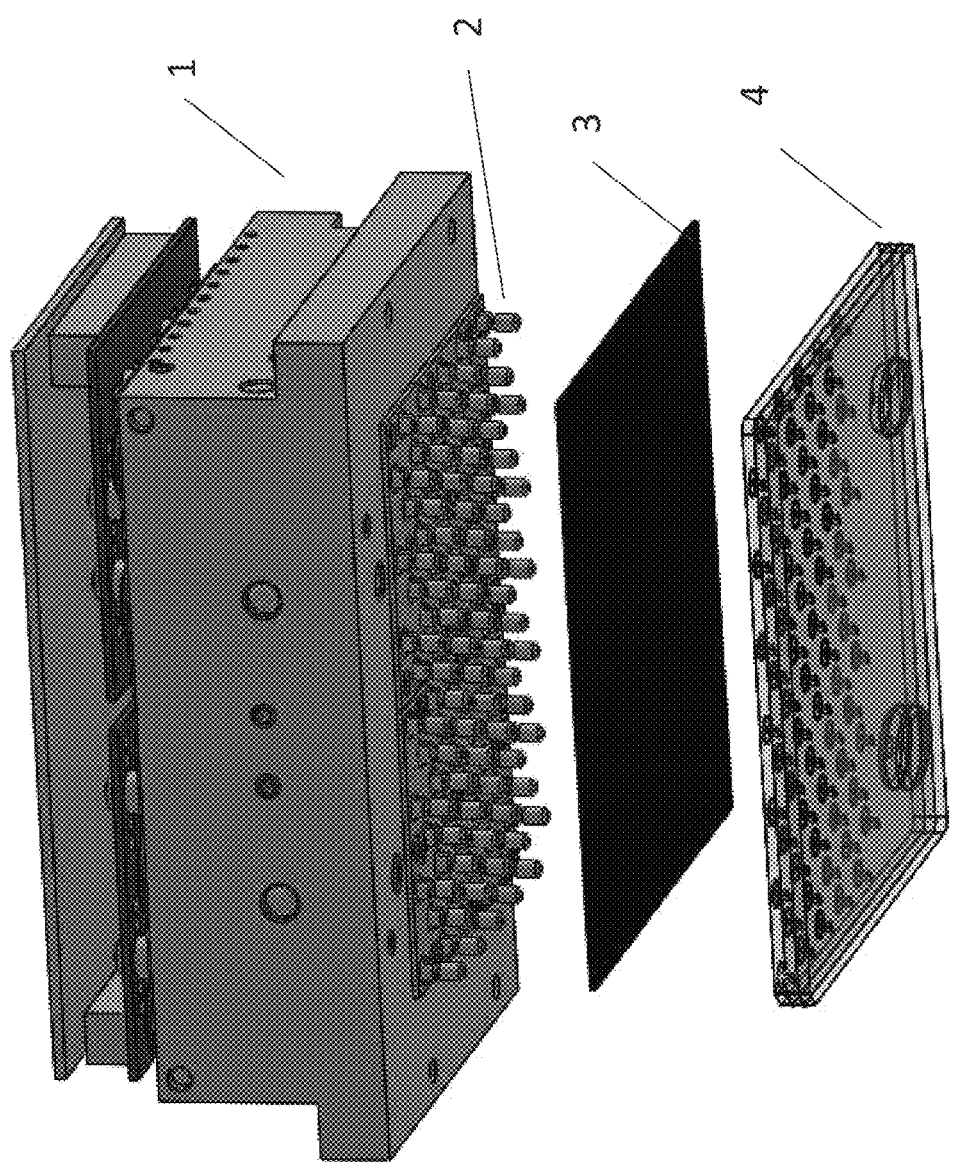

The various features of the system are shown in FIG. 1, FIG. 2, FIG. 3, FIG. 4 and FIG. 5. FIG. 1 shows a computer-aided design (CAD) rendering of the valve actuator block 1 with plungers 2, the damping layer 3 and the disposable monolithic chip 4. The term "monolith" or "monolithic" refers to a continuous piece or component or part (e.g., a monolithic chip). Alternatively, a monolith may have several components which are fitted or bonded or otherwise joined to form a continuous piece or part (e.g., monolithic piece 25.

Figure 2:
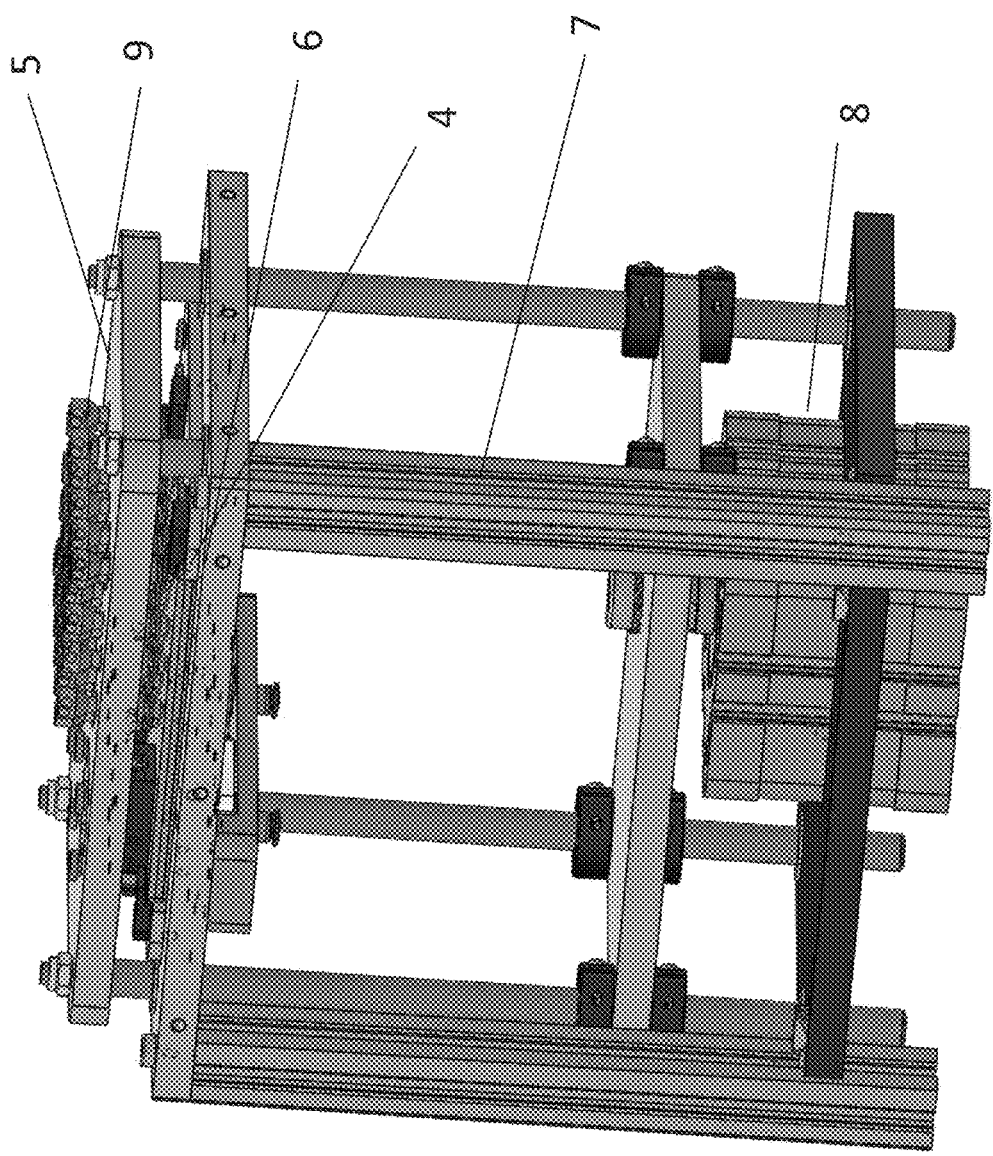
Figure 3:
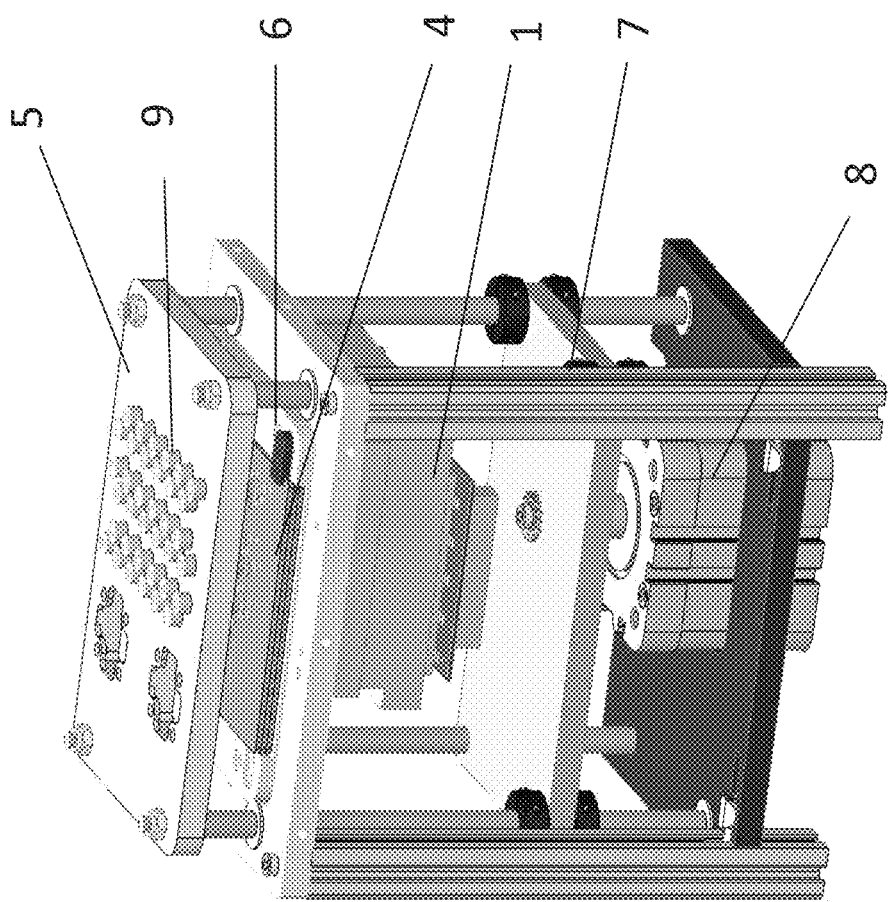
FIG. 3 shows the system of FIG. 2, now with the valve actuator block attached to the fixture 7.
Figure 5:
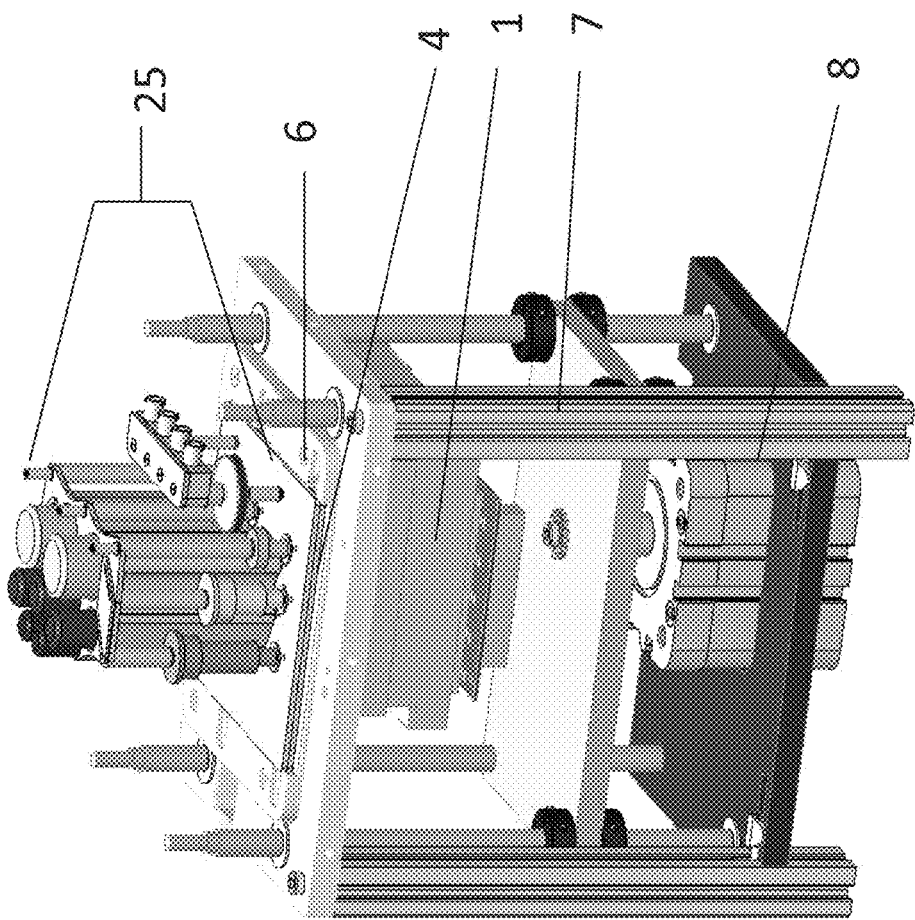
FIG. 5 shows a CAD rendering of the system of FIG. 4, now with the valve actuator block attached to the fixture 7.

Referring to FIG. 2, FIG. 3 and FIG. 5, the system comprises a fixture 7, which is a rigid work bench or stand having shelves/stacks. The components on the fixture are slid or clicked or inserted or attached in place. The fixture rigidly fixes the valve actuator block 1 and allows for alignment of the membrane valve array in chip 4 with corresponding actuators in the valve actuator block 1. The fixture also aligns the connector array 9 with the membrane valve array in the chip 4. Connections/alignment between the components in the system are made simultaneously in parallel, by a single linear motion.

The monolithic disposable chip 4 is designed for fast and easy insertion and ejection into and out of the system without the need for tools. To satisfy this requirement, the chip 4 is designed without permanent connections or dangling connections to the rest of the system. It is also spatially defined, and rigid on the length scale of acceptable valve actuator to valve misalignment, in order to allow it to be reliably and easily inserted and removed from the system. Spatially defined in this context means that the external envelope of the part and the location of its sub-components is determined by design. In contrast, an example of a piece that is not spatially defined by this definition would be three sub-components connected together by flexible tubing, since the position of the three sub-components and the shape of the tubing is not determined by design due to the flexibility of the tubing and the absence of a rigid structure to confine the flexible parts. A guiding slot 6 on the fixture allows for easy installation of the chip 4. The disposable monolithic chip consists of multiple membrane valves 10 in a two-dimensional array, multiple fluidic ports in/among the membrane valves, and a three-dimensional channel network that connects valves and fluidic ports. In the embodiment shown in FIG. 2, the two-dimensional array of valves describes valves arranged in a two-dimensional interconnection matrix and not simply a one-dimensional serial connection of valves arranged for example in a serpentine on a surface to cover a two-dimensional area. Other variations of valve arrays will be evident to one of skill in the art and such variations are contemplated within the scope of embodiments presented herein.

In some embodiments, the disposable monolithic chip is comprised of one or more layers of sheets, plates or foils, or combinations thereof. In such embodiments, the chip comprises sheets, plates or foils of polymers, glass, ceramics (such as low temperature co-fired ceramics (LTCC)), 3D printed or laser sintered materials, metals (such as steel, brass, aluminum), or combinations thereof. In one non-limiting example, the three-dimensional channel network in the chip is engineered by use of layers of polymer films/ plates/foil which have channels/grooves engraved or etched or otherwise formed on the polymeric material. Similarly, the valve seats can be machined or molded on the substrate. The layers of polymer films/plates/foil are bonded to form the final monolithic disposable chip comprising a three-dimensional network of interconnecting channels among the membrane valves.

Figure 7:
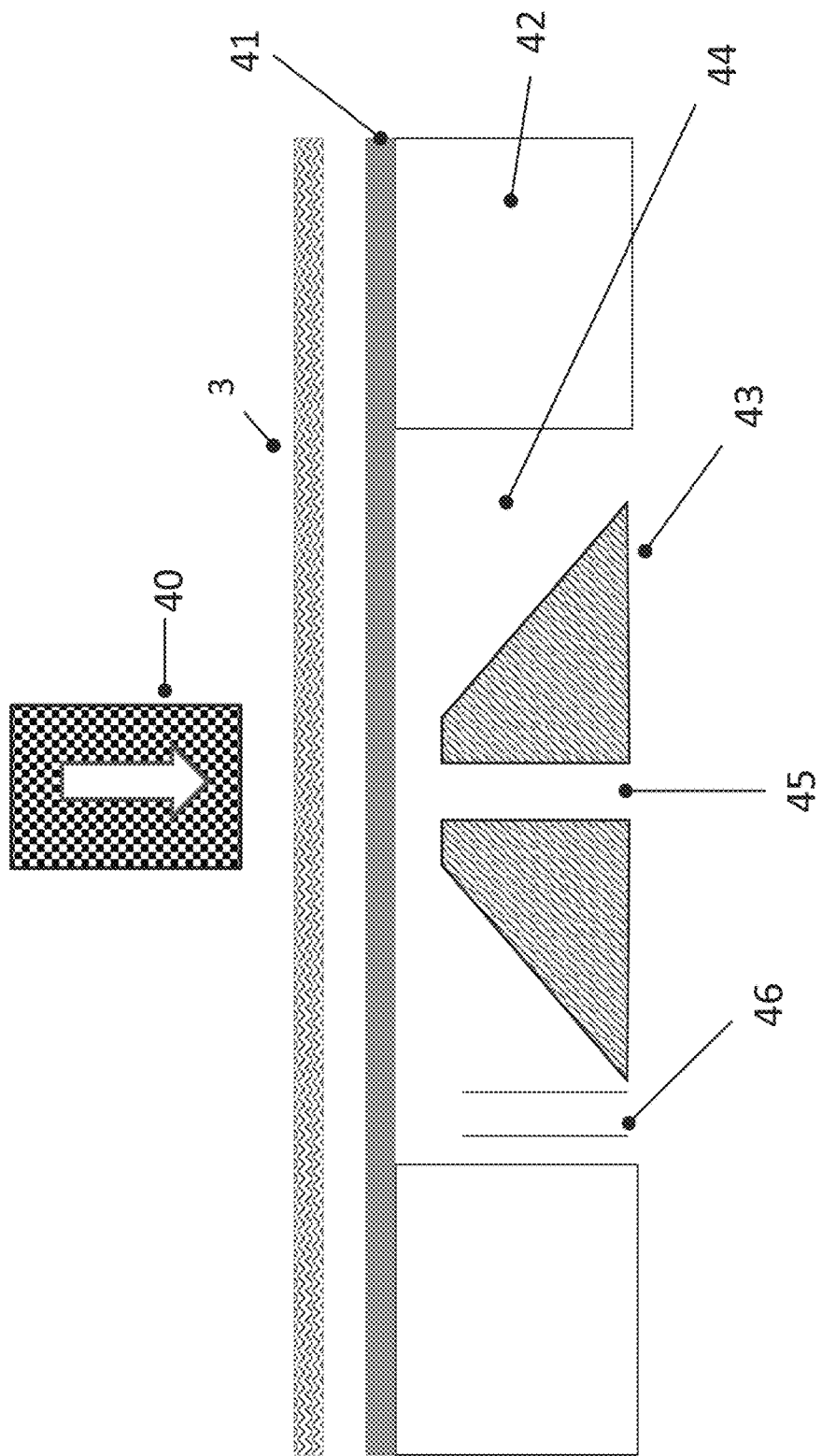
FIG. 7 shows a schematic cross section of a valve in the array.

In one group of embodiments, the membrane valves in the array comprise a central port that is isolated, or fluidically connected to a second port under the membrane, where the connection between said central port and said second port is controlled by deformation of the membrane upon actuation of the corresponding plunger in the valve actuator block. Referring to FIG. 7 and FIG. 8, each membrane valve 10 in the two-dimensional array of membrane valves on the disposable chip 4 has a central port 45, normal to the membrane, that is, on-demand, isolated or fluidically connected to a second port 46 under the membrane, by deformation of the membrane 41. The membrane 41 is deformed by pressure from one of the actuators in the actuator array. The force from the actuator is concentrated on a valve seat that is small enough in area, and of sufficiently good surface quality, to allow sealing between a membrane and a valve seat of the same material. This is achieved without plastic deformation of either the valve seat or the membrane, while minimizing the force required from the actuator in order to minimize the size of the actuator and thus increase the density of the valves in the array. A second port 46 under the membrane can be configured as either the input or output port, depending on the pressure in the main chamber under the membrane in the closed state, relative to the ambient pressure on the open external surface of the membrane.

The restoring force for the membrane 41 to return to the open state depends on the elasticity of the membrane. The restoring force of the membrane is greater than the force generated by the differential pressure across the membrane. Furthermore, in networked configurations with multiple valves connected by multiple channels where more than one channel converges at a single valve, the selection of inlet and outlet port for each membrane valve is made based on the desired application of the system. By way of example only, when utilizing the membrane valve to isolate a vacuum source through a single valve, when the membrane valve array and the interconnected channels operate in an ambient pressure of 1 Bar absolute, the lowest pressure in the system would be connected to the central port that is switched (closed or opened) by the position of the membrane. When utilizing two membrane valves in parallel, where one valve connects to a channel that must be reliably isolated from the rest of the system, the channel to be isolated should be connected to the central port of a membrane valve, regardless of pressures, to avoid flow from alternative upstream routing of channels due to differential system pressures.

For each valve 10, the internal shape of the valve region under the membrane is designed to minimize the dead volume as this region is filled or purged each time the valve is inserted into a fluid path. In conventional valves, the valve seat 43 is usually made from a hard material with the smallest area possible, in order to increase the pressure in the valve seat area when the membrane is pressed downwards towards the seat, thus improving the seal for any given force. The disposable monolithic chip with the two-dimensional membrane valve array is fabricated by molding the valve seats into the substrate (chip body) 42, and laminating a deformable membrane 41 over the valve seats. When the membrane 41 is made from a softer polymer, the hard-soft typical configuration is replicated. In some embodiments described herein, the valve seat and valve membrane in the disposable device are made from the same material and good, reproducible sealing without plastic deformation is achieved by geometric design, force, and mode of operation as described herein.

Fast actuator dynamics are required to achieve fast valve switching responses (<100 ms open to closed and open again). This type of actuator motion, independent of the type of actuator used, can result in hard impact between the actuator plungers and the valve membrane, causing accelerated fatigue and cracking of the valve membrane. When this is a problem, the problem can be solved by the insertion of a damping sheet between the actuator array and the valve array.

Accordingly, in one embodiment, the system further comprises a damping layer disposed between the valve actuator block and the disposable monolithic chip, as shown in FIG. 1. In one group of embodiments, the damping layer is reversibly deformable towards one or more membrane valve recesses in the membrane valve array, as shown in FIG. 8, when one or more plungers in the valve actuator block is actuated.

Figure 6:
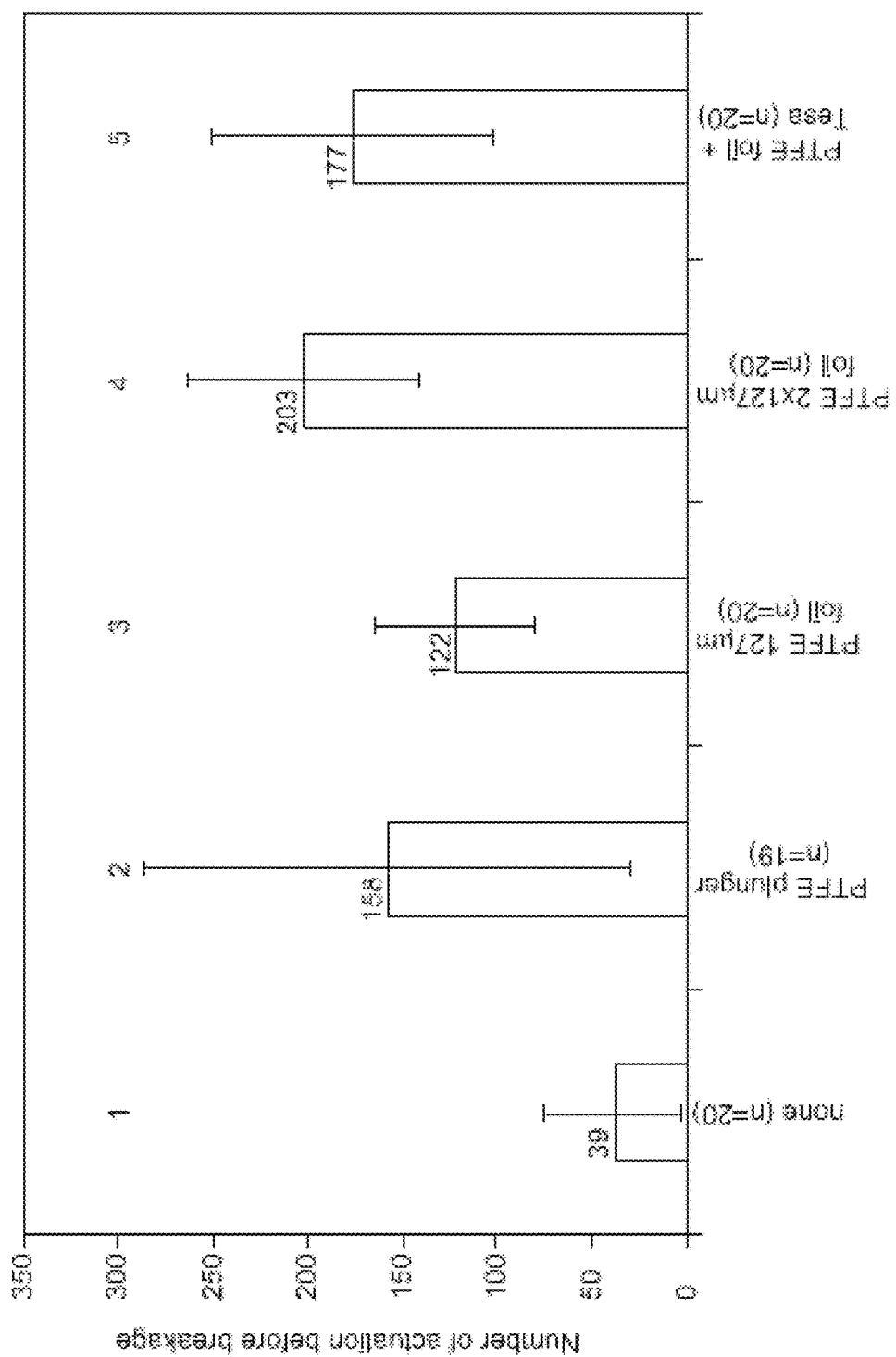
FIG. 6 shows results for a screening experiment on valve switching until failure for different configurations.

The damping film is a low-cost, scalable alternative to soft tips on each actuator plunger, and was found to increase the valve lifetime by a factor of five (measurement based on consecutive switching cycles). The problem can be further minimized by reducing the actuator stroke to its minimum, to minimize the actuator plunger momentum at the point of impact. FIG. 6 shows initial results for a screening experiment on valve switching until failure for different configurations: (1) Without a damping element, (2) PTFE tip added to plungers, (3) PTFE damping layer (127 µm thickness), (4) 2× PTFE damping layer (127 µm each), (5) PTFE damping layer (127 µm)+adhesive tape (~150 µm thickness). As can be seen from FIG. 6, the presence of the damping layer allows for a higher number of actuations before breakage.

In addition to extending the life of the membrane 41, the damping layer 3 can also be integrated in the system in a way that physically isolates the disposable monolithic chip's loading compartment from the actuator array. In some of such embodiments, the damping layer/film forms a sealed compartment such that the plungers of the valve actuator block are located on the outside of the sealed compartment and the membrane valve array is on the inside of the sealed compartment. In such embodiments, the disposable monolithic chip is the only component that is in contact with the process gases or liquids, the plungers and actuators do not contact the process gases or liquids, thereby reducing contact of the actuator machinery with corrosive fluids and reducing the need for replacing parts. Under certain failure conditions, such as a cracked or ruptured valve or chip, or a failure condition where there is an incomplete seal between the chip and the connector plate, it is possible that a process fluid leaks out of the system. In such instances, a chip compartment that is physically isolated from the actuator array by the damping layer serves the additional function of protecting the actuator array from process fluids and can also simplify the clean-up procedure.

In some embodiments, the damping layer comprises cyclic olefin co-polymer (COC), cyclic olefin polymer (COP), polyethylene (PE), polypropylene (PP), polyether ether ketone (PEEK), polytetrafluoroethylene (PTFE), ethylene tetrafluoroethylene (ETFE), polydimethylsiloxane (PDMS), polystyrene (PS), polycarbonate (PC), silicone, fluoroelastomers including and not limited to Viton® and other FKM derived materials, perfluoroelastomers including and not limited to Kalrez® and other FFKM derived materials, parylene or parylene-coated materials or combinations thereof. The damping layer typically has a thickness of about 0.05 mm to about 2 mm.

As shown in FIG. 2, FIG. 3, FIG. 4 and FIG. 5, the disposable monolithic chip 4 has a first surface comprising the two-dimensional array of membrane valves that are actuated by plungers from the valve actuator block, and a second surface operatively coupled to a connector plate 5. The connector plate 5 has connectors 9 disposed thereon. In the embodiments described herein, the connectors enable parallel fluidic connections between the membrane valves and reagent reservoirs, reaction vessels, separation columns (e.g., high pressure liquid gel chromatography columns, silica or alumina columns, ion exchange columns, and the like), filters, waste reservoirs, vacuum lines, gas lines, measurement instruments, or combinations thereof.

Figure 4:
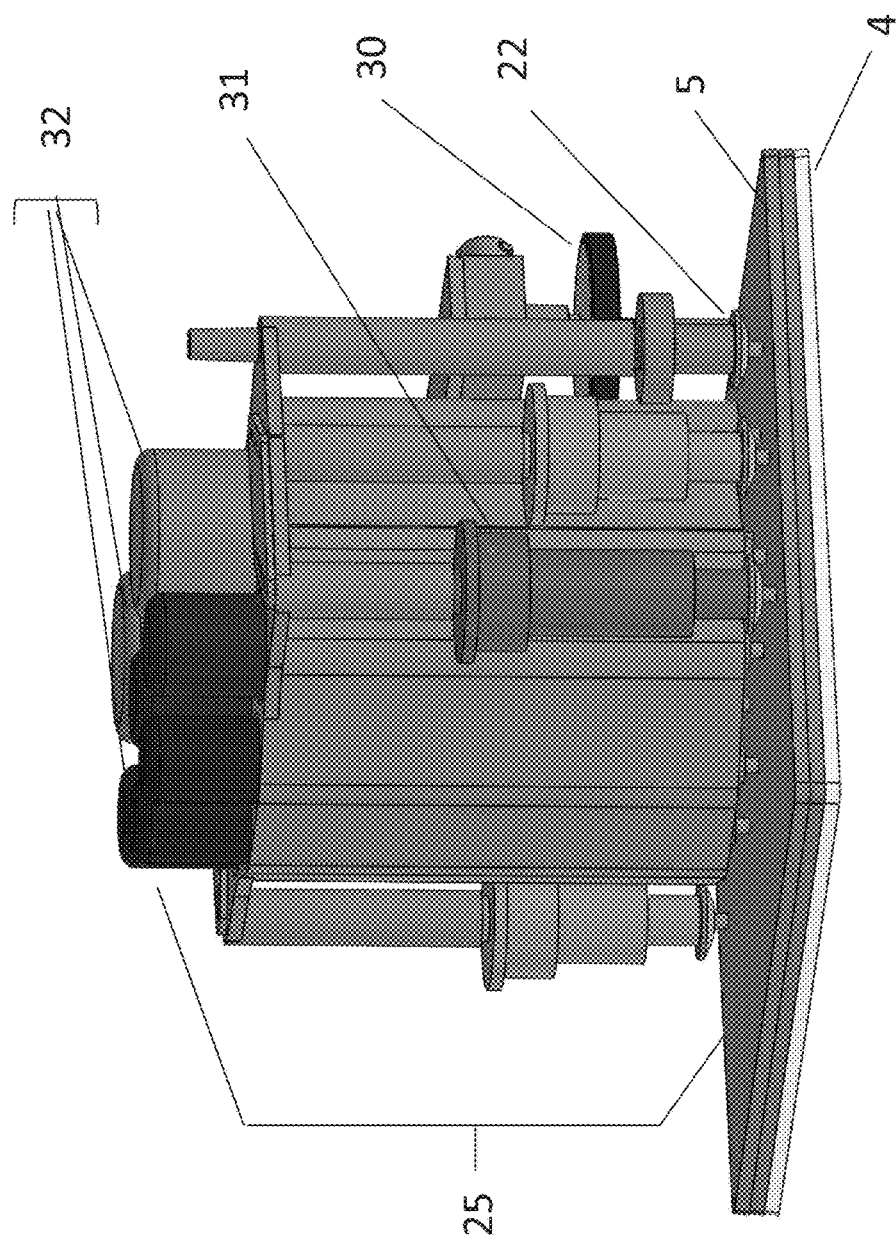
FIG. 4 shows a CAD rendering of the system in an alternate embodiment.

In one group of embodiments, the connector plate is attached to the disposable monolithic chip 4, as shown in FIG. 4 and FIG. 5. Referring to FIG. 4, the connector plate 5 is itself a monolithic piece comprising filters 30, separation column 31, solvent or reagent or waste reservoirs 32, and the like, attached via connectors 22, and is attached to the disposable monolithic chip 4 comprising the valve array. In such embodiments, the disposable monolithic chip and the connector plate with additional components attached thereto form a monolithic piece 25 which can be inserted in a guiding slot 6 on the fixture 7, as shown in FIG. 5. In such embodiments, the connector plate attached to the monolithic chip together form a single use disposable 25.

In another group of embodiments, the connector plate is not attached to the disposable monolithic chip, as shown in FIG. 2 and FIG. 3. In some of such embodiments, the connectors disposed on the connector plate are cone connectors or o-ring connectors. FIG. 2 and FIG. 3 show a disposable monolithic chip 4 in a guiding slot 6, and a connector plate 5 with connectors 9 disposed thereon. The various components of the system are attached or mounted on fixture 7. An actuator and drivetrain 8, for mechanically clamping, engaging, sealing, and locking the chip, is used to increase or reduce the separation between connector plate 5 and valve actuator block 1. When the separation is large, the disposable chip can be slid into the guiding slot 6. When the separation is reduced, the disposable chip is held in place in the fixture 7, and mechanically interfaced to the connector plate 5 and the valve actuator block 1. In this embodiment, the connector plate is reusable for multiple runs (i.e., it is not discarded with the chip).

In various embodiments, the disposable monolithic chip comprises cyclic olefin polymer (COP), cyclic olefin co-polymer (COC), polyethylene (PE), polypropylene (PP), polyether ether ketone (PEEK), fluorinated polymers including and not limited to polytetrafluoroethylene (PTFE) or ethylene tetrafluoroethylene (ETFE), polymethylmethacrylate (PMMA), silicones (such as polydimethylsiloxane (PDMS) and the like), polystyrene (PS), polycarbonate (PC), glass, ceramics (such as low temperature co-fired ceramics (LTCC)), 3D printed or laser sintered materials, metals (such as steel, brass, aluminum), or combinations thereof.

In certain cases, the valve actuator array is an electro-pneumatic array. Other actuators are contemplated within the scope of embodiments described herein, including and not limited to direct-drive plungers attached to electromagnetic solenoids, electromagnetic motors, or pneumatic, piezoelectric, hydraulic, or phase-change actuators. Alternatively, the plungers can be attached to any type of remote actuators via linkage systems or Bowden cables, thus allowing the actuator plungers to be spatially arranged without limitations imposed by the size of the actuators. The electropneumatic array consists of a two-dimensional array of 3/2 electromagnetic solenoid valves. One port is connected to the actuation pressure supply line, one port is connected to the exhaust line, and the final port is connected to the chamber of the spring-loaded pneumatic actuator piston. In the array of valves, each solenoid valve is connected to the same pressure supply and exhaust lines, but is individually addressed electrically. This arrangement reduces the number of external valve actuator array gas connections to only two, simplifying the integration of the valve actuator array and reducing the space required for gas fittings.

In some embodiments, each individual valve in the membrane valve array has a diameter ranging from about 3 mm to about 5 mm, and the valve to valve separation in the array is about 8 mm.

In some embodiments, the valve actuator block comprises individual pneumatic pistons with a pneumatic force effective diameter ranging from about 2 mm to about 15 mm and operating pressures from about 1 bar to about 10 bar pressure In any of the embodiments described above, the disposable monolithic chip is a gamma sterilized disposable monolithic chip. In any of the embodiments described above, the disposable monolithic chip is a heat sterilized disposable monolithic chip.

Also provided herein is a method for automation of fluidic processes comprising:
providing a fluidic binary switch system comprising a fixture having an attached valve actuator block and a guiding slot,
where the valve actuator block comprises a two-dimensional array of plungers, each plunger having a corresponding individually addressable actuator;
placing a disposable monolithic chip in the guiding slot, where the disposable monolithic chip comprises
(a) a two-dimensional array of membrane valves;
(b) interconnecting channels among the membrane valves; and
(c) fluidic ports for the membrane valves;
establishing parallel fluidic connections between the membrane valves and reagent reservoirs, reaction vessels, separation columns, filters, waste reservoirs, vacuum lines, gas lines, measurement instruments, or combinations thereof via connectors disposed on a connector plate;
and
executing one or more fluidic process runs on the system.

In some embodiments of the method, the fluidic process comprises serial synthesis, parallel synthesis or analysis of compounds. In some of such embodiments, the fluidic process comprises synthesis of radiopharmaceuticals. In further embodiments, the fluidic process comprises synthesis of compounds, purification or isolation of analytes from several samples in parallel, and the like.

At the point of use, the disposable monolithic chip is inserted into the fixture guiding slot, with the system sitting in an open state, where the connector plate 5, or the single use disposable 25 is in a retracted position. After the chip is fully inserted into a guiding slot in the fixture, and sized for coarse alignment, a linear actuator brings the connector plate 5 or the single use disposable 25 into contact with the chip. In this single motion, all fluidic connections are made simultaneously. At the same time the chip is fine aligned to the fixture and any other elements rigidly attached to the fixture, such as radiation detectors and optical detectors, and the chip is also clamped in position. The chip remains clamped, mechanically interfaced to the actuator block, and fluidically connected to the system until the linear actuator withdraws the connector plate 5 and the valve actuator block 1 from the chip.

When the connectors and reagent reservoirs are permanently attached to the connector plate and the disposable monolithic chip, the fixture guiding slot is designed to accept the combination of the chip, the connector plate, and reagent reservoirs. Once again, the system is in an open state at the point of insertion and the single use disposable 25 is clamped in position in a single linear motion.

In an example case of PET tracer synthesis in a typical lab situation using microfluidic membrane valves made from cyclic olefin copolymer (COC), the following are approximately representative of requirements that need to be satisfied.

The disposable monolithic chip should be made as compact as possible in the plane, to reduce the size and mass of the associated radiation shielding. Individual membrane valve diameters range from about 1 mm to about 15 mm, and the separation between valves also varies depending on the application. Within a membrane valve array, the individual valves may have the same or different diameters. By way of example only, in one instance, each individual valve in the membrane valve array has a diameter ranging from about 3 mm to about 5 mm, and the valve to valve separation in the array is about 8 mm. The force required to close the membrane valve ranges from about 1N to 100 N depending on the valve size. Normal gas pressure in the lab is 4 Bar to 10 Bar. Valve closed-open-closed cycle times are <100 ms, and in some embodiments, 50 ms.

Interconnects are required between the disposable monolithic chip and remote reagent reservoirs not directly attached to the chip. Individual pneumatic pistons within an array may have the same or different diameters with a pneumatic force effective diameter ranging from about 2 mm to about 15 mm, and operating pressures ranging from about atmospheric pressure to about 10 Bar pressure, for example, an embodiment where pistons have a pneumatic force effective diameter of about 6 mm and operate at about 5 Bar pressure.

To construct the system, a connector plate comprising conic connectors integrated in the connector plate is rigidly attached and aligned to the fixture as shown in FIG. 3. Reservoirs of reagents interface to the connector plate via tubing, capillaries, cannulas, and the like. This set up allows the chip to be easily replaced but the reagent reservoirs and the connector plate to be used multiple times. In this embodiment, as the connector plate and connectors could be a source of potential cross-contamination between different runs.

In a second similar PET tracer synthesis example, the potential cross-contamination between different runs in the aforementioned example is eliminated by cleaning or sterilizing the connector plate and connectors in-situ, using heat, radiation, or chemical cleaning and sterilization techniques.

In a third similar PET tracer synthesis example, the connector plate is permanently attached to the chip as shown in FIG. 4 and FIG. 5, and in doing so a permanent connection between reagent reservoirs and the chip is achieved through the connector plate. In this case there is no need for fine alignment between the fixture and the chip for reliable fluidic connections, as all fluidic connections are made between the chip and the connector plate which together form one single use disposable component.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A fluidic binary switch system comprising:
   a valve actuator block attached to a fixture and comprising
      a two-dimensional array of plungers, wherein each plunger comprises an individually addressable actuator; and
   a disposable monolithic chip positioned in a guiding slot on the fixture and comprising:
      a two-dimensional array of membrane valves, each membrane valve comprising a valve seat, wherein the valve seats for all the membrane valves in the two-dimensional array are in direct contact with a membrane;
      a three-dimensional channel network comprising interconnecting channels among the membrane valves; and
      fluidic ports for the membrane valves;
   wherein the fixture aligns the plungers in the valve actuator block with corresponding membrane valves in the monolithic chip.

2. The fluidic binary switch system of claim 1, further comprising a damping layer disposed between the valve actuator block and the disposable monolithic chip.

3. The fluidic binary switch system of claim 2, wherein the damping layer forms a sealed compartment such that the plungers of the valve actuator block are located on outside of the sealed compartment and the membrane valve array is on inside of the sealed compartment.

4. The fluidic binary switch system of claim 2, wherein the damping layer is reversibly deformable towards one or more membrane valve receses in the membrane valve array when one or more plungers in the valve actuator block are actuated.

5. The fluidic binary switch system of claim 2, wherein the damping layer comprises cyclic olefin co-polymer (COC), cyclic olefin polymer (COP), polyethylene (PE), polypropylene (PP), polyether ether ketone (PEEK), polytetrafluoroethylene (PTFE), ethylene tetrafluoroethylene (ETFE), polydimethylsiloxane (PDMS), polystyrene (PS), polycarbonate (PC), silicone, fluoroelastomers, perfluoroelastomers, parylene or parylene-coated materials, or combinations thereof.

6. The fluidic binary switch system of claim 1, wherein the disposable monolithic chip comprises:
   a first surface comprising the two-dimensional array of membrane valves that are actuated by plungers from the valve actuator block; and
   a second surface operatively coupled to a connector plate.

7. The fluidic binary switch system of claim 6, wherein the connector plate is attached to the disposable monolithic chip.

8. The fluidic binary switch system of claim 7, wherein the guiding slot on the fixture accepts the connector plate.

9. The fluidic binary switch system of claim 6, wherein the connector plate is not attached to the disposable monolithic chip.

10. The fluidic binary switch system of claim 6, wherein the connector plate comprises an array of connectors disposed thereon.

11. The fluidic binary switch system of claim 10, wherein the connectors are cone connectors or o-ring connectors.

12. The fluidic binary switch system of claim 10, wherein the connectors enable parallel fluidic connections between the membrane valves and reagent reservoirs, reaction vessels, separation columns, filters, waste reservoirs, vacuum lines, gas lines, measurement instruments, or combinations thereof.

13. The fluidic binary switch system of claim 1, wherein the disposable monolithic chip comprises one or more layers of sheets, plates, foils, or combinations thereof.

14. The fluidic binary switch system of claim 13, wherein the disposable monolithic chip comprises cyclic olefin polymer (COP), cyclic olefin co-polymer (COC), polyethylene (PE), polypropylene (PP), polyether ether ketone (PEEK), polytetrafluoroethylene (PTFE), ethylene tetrafluoroethylene (ETFE), polymethylmethacrylate (PMMA), polystyrene (PS), polycarbonate (PC), a silicone, glass, ceramics, 3D printed or laser sintered materials, metals, or combinations thereof.

15. The fluidic binary switch system of claim 1, wherein the membrane valves comprise a central port that is isolated, or fluidically connected to a second port under the membrane, wherein the connection between the central port and the second port is controlled by deformation of the membrane up on actuation of corresponding plungers in the valve actuator block.

16. The fluidic binary switch system of claim 1, wherein the valve actuator array is an electropneumatic array.

17. The fluidic binary switch system of claim 1, wherein each individual valve in the membrane valve array has a diameter ranging from about 1 mm to about 15 mm.

18. The fluidic binary switch system of claim 1, wherein the valve actuator block comprises individual pneumatic pistons with a pneumatic force effective diameter ranging from about 2 mm to about 15 mm and operating at pressures ranging from about 1 bar to about 10 bar.

19. A method for automation of fluidic processes comprising:
   providing a fluidic binary switch system, wherein the fluidic binary switch system comprises a fixture having an attached valve actuator block and a guiding slot, wherein the valve actuator block comprises a two-dimensional array of plungers, each plunger having a corresponding individually addressable actuator;
   placing a disposable monolithic chip in the guiding slot, wherein the disposable monolithic chip comprises:
      a two-dimensional array of membrane valves, each membrane valve comprising a valve seat, wherein the valve seats for all the membrane valves in the two-dimensional array are in direct contact with a membrane;
      a three-dimensional channel network comprising interconnecting channels among the membrane valves; and
      fluidic ports for the membrane valves;
   establishing parallel fluidic connections between the membrane valves and reagent reservoirs, reaction vessels, separation columns, filters, waste reservoirs, vacuum lines, gas lines, measurement instruments, or combinations thereof via connectors diposed on a connector plate; and
   executing one or more fluidic process runs on the fluidic binary switch system.

20. The method of claim 19, wherein the one or more fluidic process comprises serial synthesis, parallel synthesis, or analysis of compounds.

* * * * *